United States Patent
Tuke et al.

(10) Patent No.: US 8,372,155 B2
(45) Date of Patent: Feb. 12, 2013

(54) ACETABULAR CUP PROSTHESIS AND METHOD OF FORMING THE PROSTHESIS

(75) Inventors: Michael Antony Tuke, Guildford (GB); Andrew Clive Taylor, Nr Chichester (GB)

(73) Assignee: Finsbury (Development) Limited, Leatherhead (GB)

( * ) Notice: Subject to any disclaimer, the term of this patent is extended or adjusted under 35 U.S.C. 154(b) by 0 days.

(21) Appl. No.: 12/572,039

(22) Filed: Oct. 1, 2009

(65) Prior Publication Data

US 2010/0087930 A1  Apr. 8, 2010

(30) Foreign Application Priority Data

Oct. 7, 2008 (GB) .................................. 0818326.1
Oct. 9, 2008 (GB) .................................. 0818505.0

(51) Int. Cl.
*A61F 2/32* (2006.01)
(52) U.S. Cl. .................................. 623/22.21; 623/22.32
(58) Field of Classification Search ............... 623/22.21, 623/22.2
See application file for complete search history.

(56) References Cited

U.S. PATENT DOCUMENTS

| | | | | |
|---|---|---|---|---|
| 4,166,292 A | * | 9/1979 | Bokros | ........................ 623/21.18 |
| 4,262,369 A | | 4/1981 | Roux | |
| 4,813,959 A | | 3/1989 | Cremascoli | |
| 5,405,402 A | | 4/1995 | Dye et al. | |
| 5,549,678 A | * | 8/1996 | Prostkoff | .................... 623/17.19 |
| 5,702,478 A | | 12/1997 | Tornier | |
| 5,879,397 A | | 3/1999 | Kalberer et al. | |
| 6,022,357 A | | 2/2000 | Reu et al. | |
| 6,096,083 A | | 8/2000 | Keller et al. | |
| 6,475,243 B1 | | 11/2002 | Sheldon et al. | |
| 6,589,284 B1 | | 7/2003 | Silberer | |
| 7,267,693 B1 | * | 9/2007 | Mandell et al. | ............. 623/22.28 |
| 2002/0068980 A1 | | 6/2002 | Serbousek et al. | |
| 2005/0240276 A1 | | 10/2005 | Shea et al. | |
| 2005/0288793 A1 | | 12/2005 | Dong et al. | |
| 2006/0190089 A1 | | 8/2006 | Montoya et al. | |
| 2009/0005878 A1 | | 1/2009 | Tuke et al. | |
| 2009/0005879 A1 | | 1/2009 | Tuke et al. | |

FOREIGN PATENT DOCUMENTS

| | | |
|---|---|---|
| DE | 16940747 A1 | 2/1998 |
| DE | 10006098 | 2/1999 |
| EP | 0532439 A2 | 3/1993 |
| EP | 0630624 A1 | 12/1994 |
| EP | 0694294 A1 | 1/1996 |
| EP | 1290992 A1 | 12/2003 |
| EP | 1433443 | 6/2004 |
| EP | 1433443 A1 * | 6/2004 |
| EP | 2008619 A2 | 12/2008 |
| EP | 2008620 A2 | 12/2008 |
| FR | 2735356 A1 | 12/1996 |
| FR | 2749162 A1 | 12/1997 |
| FR | 2825911 A1 * | 12/2002 |

OTHER PUBLICATIONS

Valery I. Rudnev, Joining Components by Inductive Heating, Part II, Heat Treating Process, May/Jun. 2005, pp. 25-27.*
European Search Report for 09169709.4, dated Feb. 4, 2010, 6 pages.

* cited by examiner

*Primary Examiner* — Bruce E Snow
*Assistant Examiner* — Brian Dukert
(74) *Attorney, Agent, or Firm* — Armstrong Teasdale LLP

(57) ABSTRACT

An acetabular cup prosthesis comprising an acetabular cup having a rim and comprising a metal band applied around the outer circumference of the acetabular cup prosthesis and adjacent to said rim.

7 Claims, 2 Drawing Sheets

ACETABULAR CUP PROSTHESIS AND METHOD OF FORMING THE PROSTHESIS

FIELD OF THE INVENTION

The present invention relates to a prosthesis. More particularly, it relates to a preassembled acetabular component for a hip prosthesis and a process for the production thereof.

BACKGROUND OF THE INVENTION

The efficient functioning of the hip joint is extremely important to the well-being and mobility of the human body. Each hip joint is comprised by the upper portion of the femur which terminates in an offset bony neck surmounted by a ball-headed portion which rotates within the acetabulum in the pelvis. Diseases such as rheumatoid- and osteo-arthritis can cause erosion of the cartilage lining of the acetabulum so that the ball of the femur and the hip bone rub together causing pain and further erosion. Bone erosion may cause the bones themselves to attempt to compensate for the erosion which may result in the bone becoming misshapen.

Operations to replace the hip joint with an artificial implant are well-known and widely practiced. Generally, the hip prosthesis will be formed of two components, namely: an acetabular component which lines the acetabulum; and a femoral component which replaces the femoral head. The femoral component may be total femoral head replacement in which case the component includes a head, neck and a stem which in use is inserted into the end of a prepared femur. Alternatively, where appropriate, the femoral head component may be a resurfacing prosthesis which is attached to the head of the femur once it has been suitably machined.

In an operation to insert a prosthetic acetabulum in a patient's pelvis the surgeon first uses a reamer to cut a cavity of appropriate size in the patient's pelvis. An acetabular cup is then inserted into the cavity. By "appropriate size" is meant a size which is selected by the surgeon as being the most appropriate for that particular patient. Normally, it is desirable to retain as much of the original healthy bone surface as possible.

Commercially available acetabular cups are sold in a range of sizes to suit the needs of individual patients. Generally, acetabular cups are available in sizes of from 42 mm to 62 mm diameter with 2 mm increments between neighboring sizes.

There are a number of different types of prosthetic acetabular cups. One type of cup is those made from polyethylene. They are generally cemented into the acetabulum and require only light pressure to seat them in the cement.

One alternative cup type has a polyethylene liner unit for articulation with the femur and a metal shell for insertion into the pelvic cavity. These cups with metal shells may be implanted without cement such that they rely on a jam fit between the metal shell and the patient's acetabulum. However, in some arrangements, screws may be used to secure the cup shell in position in the pelvis before the liner is applied into position. The insertion of the metal shell into the pelvis requires considerable force. As the surgeon applies this force, there is a risk that the metal shell can become damaged or deformed. There is also a possibility that during the application of the force, the shell may be moved so that it is not in the optimum alignment in the acetabulum. Often the metal shells have outer surfaces or coatings which encourage bone to grow into them over time.

With this type of prosthesis, the polyethylene liner unit is snapped or screwed into the metal shell after the metal shell has been seated in the acetabulum. Thus the inner surface of the liner forms the socket part of the joint.

More recently, ceramics have been used to as an alternative to the plastics liner. In this arrangement, the metal shell, which is generally formed from titanium and which is of a similar thickness to the arrangement in which a polyethylene liner is used, is inserted into the acetabulum. The ceramic liner is then inserted into the shell. It can be difficult for the liner to be accurately aligned in the shell. In addition, this insertion of the liner does require the application of a considerable force which is usually applied by the surgeon using a mallet often via an insertion tool. Considerable force is generally required to achieve a successful interface. However, this force can damage the ceramic liner.

In order to get an optimum fit, it is necessary that the forces applied for both the insertion of the metal shell and for the ceramic liner are appropriate but not excessive. One problem however, is that to date there has been no understanding as to what forces are appropriate nor is there a means to ensure that the correct force is applied.

The surgeon is not generally able to apply a controlled amount of force applied. Some surgeons may not apply sufficient force in one hit and it may be necessary for a plurality of hits to be used. These may not all strike at the same angle and may not each apply the same force. Other surgeons may apply a much greater single strike. The force applied by the surgeon on, for example, an insertion tool may vary considerably and can be of the order of about 3 to 5 kN but can also be much higher and may even be of the order of about 35 kN.

Whilst very large forces may only be applied for small moments in time, of the order of seconds or fractions of a second, forces of this magnitude, or a plurality of forces of smaller magnitude may cause the shell to be deformed as it is inserted into the acetabulum. This is a particular risk in those arrangements where the thickness of the shell is only from about 1 mm to about 3 mm thick. If the shell is deformed, it can become difficult or even impossible to insert the liner.

Additionally or alternatively, the liner may be incorrectly seated in the shell which can lead to various disadvantages. Not only is there a risk that where a portion of the liner stands above the rim of the cup, a point of irritation can be produced but also, there is a risk that material, such as wear debris, may congregate against the raised portion of the liner or against the wall of the cup in the area where the liner sits below the rim. This accumulation of debris may provide a site for postoperative infection. Even if the liner is correctly located and the shell is not deformed during the assembly process, it may become deformed on insertion of the prosthesis into the pelvis such that the shell may become spaced from the liner over at least a portion of the prosthesis.

Even if the surgeon is able to accurately seat the liner in the cup, there is a risk that during assembly debris may be caught between the liner and the cup which may effect the wear properties of the prosthesis. A further problem associated with the presence of debris, which may include fluids such as blood or fat, between the shell and liner is that in use, in vivo the presence of the debris may cause the shell and liner to move apart.

Without wishing to be bound by any particular theory, it will be understood where the shell and ceramic liner are held together by friction, debris, in particular fatty substances or blood, can interfere with the frictional interface between the outer surface of the liner and the inner surface of the shell such that there is a propensity for the liner to move out of the shell.

A further problem which may be encountered is that while inserting the liner in the shell it may become damaged. If this damage is a chip or crack on the outer surface of the liner, i.e.

on the surface adjacent to the surface of the shell, its presence may not be noticed by the surgeon during assembly. However, its existence will be a point of weakness which can result in the prosthesis failing in use.

One solution that has been proposed is to provide a preassembled unit acetabular cup prosthesis comprising: an outer shell; and a ceramic liner located within the shell. In one arrangement, the preassembled unit may be assembled ex-vivo under a controlled force selected to optimise the pre-stressing of the components of the prosthesis.

This arrangement provides acetabular components which reduces the risk of liner misplacement and which has enhanced life expectancy arising, in part, through improved resistance to damage caused during impaction into the acetabulum. It is also desirable to provide an acetabular cup prosthesis which can be easily handled and inserted during surgery without damage to the acetabular cup prosthesis and which minimizes the risk of debris being trapped between the cup and the liner.

Examples of such preassembled acetabular cup can be found in copending European applications 08103811.9 and 08103809.3 filed on 2 May 2008. Whilst the arrangements describe various arrangements which address the aforementioned problems, there is a need for alternative arrangements.

In certain arrangements it may be desirable to provide an acetabular cup prosthesis which is made substantially from ceramic.

Whilst acetabular cup prosthesis made from ceramic offer various advantages, they may suffer from various disadvantages. The ceramic may not have sufficient strength to withstand the rigors of insertion. Further even if the ceramic cup can be successfully inserted in the pelvis without damage, due to the structure of the surface there may be little or no torsional stability.

Even if the acetabular cup does include a thin metal shell, there may be a need to provide additional strength or additional torsional stability.

SUMMARY OF THE INVENTION

Thus according to the present invention there is provided an acetabular cup prosthesis comprising an acetabular cup having a rim and comprising a metal band applied around the outer circumference of the acetabular cup prosthesis and adjacent to said rim.

The presence of the metal band applied around the outer circumference of the acetabular cup prosthesis and adjacent the rim thereof provides additional strength to the prosthesis and in particular provides the required level of hoop compression.

The acetabular cup of the present invention may be formed of any suitable material. In a preferred embodiment the suitable material will be a ceramic. For the purposes of this application, the term "ceramic" should be construed as meaning not only true ceramic materials but also other materials which display ceramic-like properties. Ceramic-like properties for the purposes of the present invention are those where strength, stiffness and rigidity are similar to those of ceramics. Examples of suitable materials include glasses. In one arrangement a metal shell may be provided.

The prosthesis of the present invention provides a prosthesis with improved properties over prior art prosthesis. In particular, the prosthesis of the present invention has improved resistance to fracture. In particular where the cup is a ceramic cup or includes a ceramic liner, the presence of the band will serve to pre-stress the ceramic. This pre-stressing occurs during the controlled assembly process. Unstressed ceramic liners such as those of the prior art, are prone to fracture in use. Stressing of the components of the prosthesis is discussed in more detail below.

The band of the prosthesis is preferably made from metal. Any suitable metal may be used, with titanium being particularly preferred. Cobalt/chromium may also be used. The outer surface of the band may be provided with one or more ribs extending away from the cup. In use these ribs will interact with the pelvis to provide the required torsional stability. In one arrangement one or more, preferably three, ribs may be located at a plurality of points around the circumference of the band. In one arrangement one or more, preferably three ribs, may be located at three equally spaced positions around the circumference.

The ribs may be of any suitable configuration. Where there is one or more ribs present, the ribs may be of the same or of different configurations. In one arrangement, the or each rib may be a longitudinal extension.

In one arrangement, the band may be configured on its out surface to promote bone integration. In one arrangement, the outer surface may be coated with a bone growth promoting material such as hydroxyapatite.

In the embodiment where a shell is used, this may be coated on its outer surface with material to promote bone integration. In one arrangement, the outer surface may be coated with a bone growth promoting material such as hydroxyapatite.

Although not preferred, where a shell is used it may be a titanium shell. If used, the titanium shell has a thickness in the region of about 1 mm to about 3 mm.

The ceramic cup or liner may be formed of any material which has acceptable biocompatibility, hardness and wear resistance. Suitable ceramic materials include silicon nitride, doped silicon nitride, an alumina-zirconia ceramic, yttria, stabilized zirconia, ceria, stabilized zirconia, zirconia ceramics, alumina ceramics, oxinium or mixtures thereof. The thickness of the ceramic cup or liner is preferably in the region of from about 2 mm to about 5 mm.

Where the band is applied directly to the outer surface of a ceramic cup, the ceramic will generally be shaped in the region of the rim where the band is applied such that when the band is in position, the external profile of the prosthesis (ignoring any ribs or other biting configurations) will correspond to that of a ceramic cup prosthesis not having a band. Thus the cup with the band will still have the approximately hemispherical outer configuration.

It will therefore by understood that the thickness of the band will generally be of the order of a few millimeters. The surface of the band which will be in contact with the cup will generally be flat whereas the outer surface of the band may be curved and as such the shape of the band in cross-section may be D-shaped. At the thickest point it may have a thickness of the order of about 1 mm to about 3 mm.

The band may be applied to the acetabular cup by any suitable means. In one arrangement, it may be press fitted onto the cup. Since the band is a tight fit on the cup press fitting onto the cup may present difficulties. In one arrangement, the band may be heated to allow it to be correctly fitted. In one arrangement, the heating may be by induction heating. A benefit of induction heating is that only the metal band will be effected and the ceramic cup will not be heated. The induction heating may be carried out by any suitable means. The press fit may require load to be applied. The load required may depend on the temperature to which the band is heated. In one arrangement, heating may be to from about 500 to about 700 C. In one arrangement approximately 5 kN load may be used for the press-fitting.

Thus according to a second aspect of the present invention there is provided a process for forming the acetabular cup prosthesis of the above first aspect comprising the step of heating the band before applying it to the cup.

Once the band has cooled, the loading of the band on the cup will generally act to pre-stress the cup in an optimum manner such that separation between the band and the cup will not occur. In this connection it will be understood that the band being metal is strong in hoop tension whereas the ceramic cup is strong in hoop compression. With the pre-stressing of the present invention, the tensions are optimised. In particular, the residual stress in the ceramic may be engineered to a value that optimises performance and is compressive. In addition, the compressive interface between the two components is maintained throughout the entirety of the loading of the prosthesis in vivo.

A further advantage of the present invention is that the acetabular cup prosthesis of the present invention has sufficient strength to withstand the forces supplied during the insertion of the prosthesis into the acetabulum without damage, distortion or separation of the band from the cup. In particular, and surprisingly, the sphericity of the prosthesis is substantially maintained even though the diameter is reduced due to the localised compression at the rim of the liner.

The prosthesis of the present invention may be provided with an impaction cap. The impaction cap may be pre-assembled with the prosthesis as described in EP2008618 which is incorporated herein by reference. In one arrangement the impaction cup is configured such that the force applied to impact the prosthesis into the acetabulum is directed via the ceramic cup so that any shock passing through the metal band is minimised.

BRIEF DESCRIPTION OF THE DRAWINGS

The present invention will now be described, by way of example, with reference to the accompanying drawings in which.

DETAILED DESCRIPTION OF THE INVENTION

Figure 1:
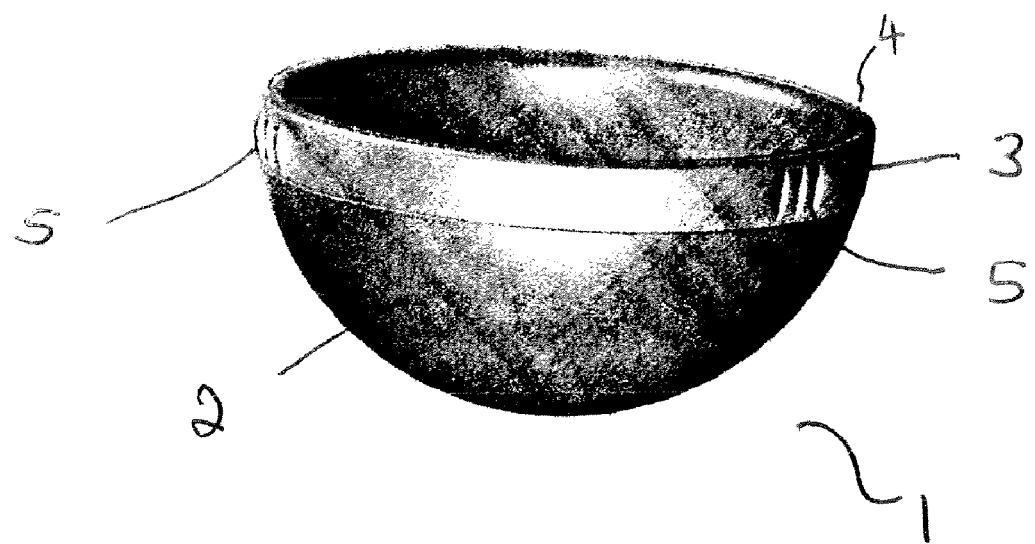
FIG. 1 is a perspective view of the acetabular cup prosthesis of the present invention.

As illustrated in FIG. 1, the prosthesis 1 of the present invention comprises a cup 2 and a titanium band 3 located around the external surface of the cup and adjacent to the rim 4 of the cup 2. Ribs 5 are located on the external surface of the band and are configured such that when located in the pelvis torsional movement of the cup in the pelvis is resisted.

Figure 2:
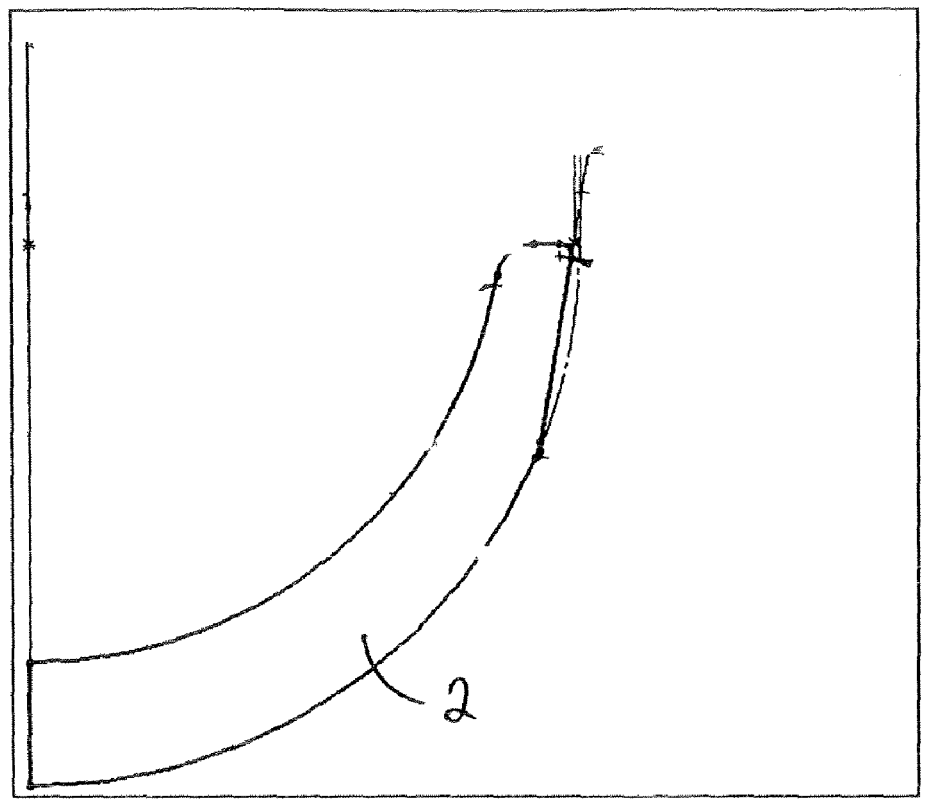
FIG. 2 is a schematic diagram of a cross section through a cup prepared to accept the band.
Figure 3:
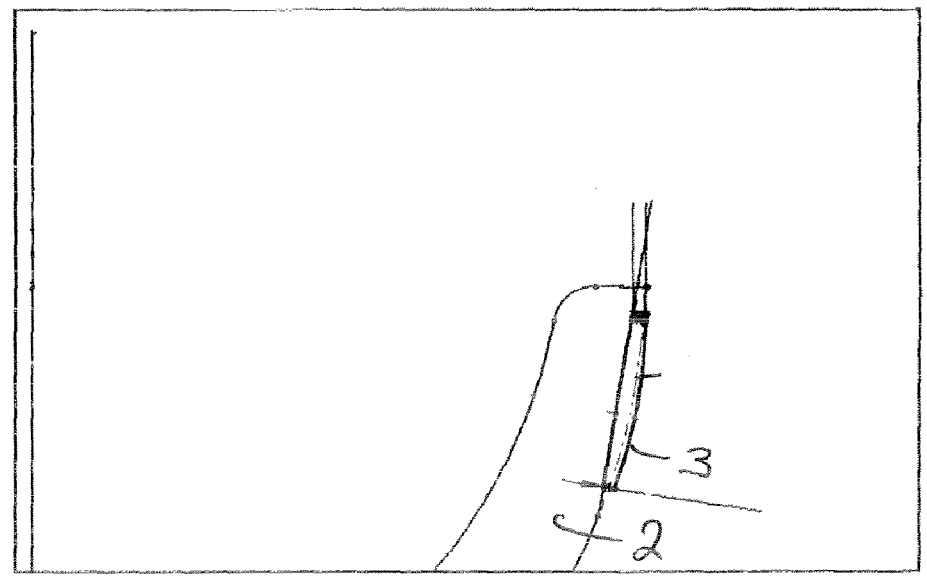
FIG. 3 is a schematic diagram of a cross section through a portion of an acetabular cup prosthesis of the present invention including the band.

The shape of the cup 2 before the band 3 is applied is illustrated schematically in FIG. 2. As illustrated in FIG. 3, the band 3 is shaped so that the hemispherical external surface of the cup is completed.

What is claimed is:

1. An acetabular cup prosthesis comprising a ceramic acetabular cup having a rim and a metal band being D-shaped in cross-section and being applied around an outer circumference of the acetabular cup prosthesis and adjacent to said rim, said metal band providing hoop compression to said acetabular cup.

2. The acetabular cup prosthesis according to claim 1 wherein the metal band is titanium.

3. The acetabular cup prosthesis according to claim 1 wherein the outer surface of the band is provided with ribs extending away from the cup.

4. The acetabular cup prosthesis according to claim 1 wherein the band at the thickest point has a thickness of from about 1 mm to about 3 mm.

5. A method of forming the acetabular cup prosthesis of claim 1 wherein the band is press fitted onto the cup.

6. The method according to claim 5 wherein the band is heated at least one of prior to and during press fitting.

7. The method according to claim 6 wherein the heating is achieved by induction heating.

* * * * *